US010195309B2

(12) United States Patent
Ginty et al.

(10) Patent No.: US 10,195,309 B2
(45) Date of Patent: Feb. 5, 2019

(54) INJECTABLE SCAFFOLD COMPOSITION

(75) Inventors: Patrick Ginty, Nottingham (GB); Robin Andrew Quirk, Nottingham (GB); Kevin Morris Shakesheff, Nottingham (GB)

(73) Assignee: LOCATE THERAPEUTICS LIMITED, Nottingham (GB)

( * ) Notice: Subject to any disclaimer, the term of this patent is extended or adjusted under 35 U.S.C. 154(b) by 0 days.

(21) Appl. No.: 12/525,195

(22) PCT Filed: Feb. 1, 2008

(86) PCT No.: PCT/GB2008/000329
§ 371 (c)(1),
(2), (4) Date: Oct. 12, 2009

(87) PCT Pub. No.: WO2008/093094
PCT Pub. Date: Aug. 7, 2008

(65) Prior Publication Data
US 2010/0063175 A1    Mar. 11, 2010

(30) Foreign Application Priority Data
Feb. 1, 2007 (GB) .................................. 0701896.3

(51) Int. Cl.
*A61F 2/02*       (2006.01)
*A61L 27/26*      (2006.01)
(Continued)

(52) U.S. Cl.
CPC ............ *A61L 27/502* (2013.01); *A61L 27/26* (2013.01); *A61L 27/38* (2013.01); *A61L 27/50* (2013.01);
(Continued)

(58) Field of Classification Search
CPC ........ A61L 26/26; A61L 27/502; A61L 27/54; A61L 27/58; C08L 67/04; C08L 71/02
(Continued)

(56) References Cited

U.S. PATENT DOCUMENTS 5,565,215 A * 10/1996 Gref et al. .................... 424/501
5,922,357 A *  7/1999 Coombes ............... A61K 9/146
                                                              424/451
(Continued)

FOREIGN PATENT DOCUMENTS

WO    WO2004084968 A    10/2004
WO    WO2007068489 A     6/2007

OTHER PUBLICATIONS

Product brochure for Pluronics by BASF Chemical Company, 3 pages, Downloaded on Mar. 27, 2014.*
(Continued)

*Primary Examiner* — Tae H Yoon
(74) *Attorney, Agent, or Firm* — Procopio, Cory, Hargreaves & Savitch LLP

(57) ABSTRACT

A composition comprising polymer particles and a carrier, wherein the polymer particles are a mixture of at least a first polymer and a second polymer, wherein the first polymer is at least partially soluble or dispersible in the carrier, and wherein the polymer particles are arranged such that they can join together to form a scaffold of polymer particles, and wherein the composition is administrable to a human or non-human animal.

19 Claims, 6 Drawing Sheets

(51) Int. Cl.
    *A61L 27/44* (2006.01)
    *A61L 27/58* (2006.01)
    *A61L 27/50* (2006.01)
    *A61L 27/38* (2006.01)
    *A61L 27/54* (2006.01)
    *A61L 27/60* (2006.01)

(52) U.S. Cl.
    CPC .............. *A61L 27/54* (2013.01); *A61L 27/58* (2013.01); *A61L 27/60* (2013.01); *A61L 2300/602* (2013.01); *A61L 2400/06* (2013.01)

(58) Field of Classification Search
    USPC ............ 523/113; 424/501; 524/537; 514/785
    See application file for complete search history.

(56) References Cited

U.S. PATENT DOCUMENTS

| | | | | |
|---|---|---|---|---|
| 6,201,072 | B1* | 3/2001 | Rathi et al. | 525/415 |
| 7,230,065 | B2* | 6/2007 | Hale et al. | 528/271 |
| 7,501,179 | B2* | 3/2009 | Song et al. | 428/402 |
| 7,750,091 | B2* | 7/2010 | Maljkovic et al. | 525/390 |
| 7,915,351 | B2* | 3/2011 | Dawkins et al. | 525/417 |
| 8,372,895 | B2* | 2/2013 | Friess et al. | 523/113 |
| 2004/0018238 | A1* | 1/2004 | Shukla | A61K 9/0019 424/486 |
| 2004/0022861 | A1* | 2/2004 | Williams et al. | 424/489 |
| 2005/0048123 | A1* | 3/2005 | Su et al. | 424/486 |
| 2006/0024377 | A1* | 2/2006 | Ying et al. | 424/489 |
| 2007/0178159 | A1* | 8/2007 | Chen et al. | 424/484 |
| 2013/0101656 | A1* | 4/2013 | Su et al. | 424/422 |

OTHER PUBLICATIONS

Product brochure for Pluronics L 31 by Sigma-Aldrich, 3 pages, Downloaded on Apr. 2, 2014.*
USFDA Guideline for Polyethylene Glycols for Inactive Ingredient Search for Approved Drug Products down loaded on Nov. 19, 2007 from http://www.accessdata.fda.gov/scripts/cder/iig/getiigWEB.cfm. 12 pages.*
International Search Report and Written Opinion of the International Searching Authority for PCT/GB2008/000329 dated Jul. 17, 2009, 18 pages.
Hedberg E L et al. Controlled release of an osteogenic peptide from injectable biodegradable polymeric composites, Journal of Controlled Release, Elsevier, Amsterdam, NL, vol. 84, No. 3, Dec. 5, 2002 (Dec. 5, 2002), pp. 137-150, XP004395985 ISSN: 0168-3659.
Baiardo, Massimo et al., Thermal and Mechanical Properties of Plasticized Poly (L-lactic acid), Journal of Applied Polymer Science, 2003, pp. 1731-1738, vol. 90, Wiley Periodicals, Inc.
Dowwolff Cellulosics, Tablet Coating A Technical Review, pp. 1-17, Trademark of the Dow Chemical Company.

* cited by examiner

INJECTABLE SCAFFOLD COMPOSITION

CROSS REFERENCE TO RELATED APPLICATIONS

This is a 371 National Stage of International Application No. PCT/GB08/00329, filed on Feb. 1, 2008, claiming priority based on United Kingdom Patent Application No. 0701896.3, filed on Feb. 1, 2007, the entire disclosures each of which are incorporated herein by reference.

The present invention relates to compositions and methods for producing tissue scaffolds.

Tissue scaffolds, or matrices, preferably have the structural and functional properties needed to allow them to be used to replace or repair damaged, missing, or poorly functioning components, such as tissues, in human or non-human animals. A tissue scaffold may be made from naturally occurring or synthetic materials, or a combination of these. The scaffold may aid and/or direct the growth of cells migrating from surrounding tissue or of cells seeded within the scaffold, providing a substrate for cell attachment, proliferation, differentiation and migration. Scaffolds may also act as a conduit for, or barrier to, the passage of material through an area where they are located. Scaffolds may also serve as a reservoir of useful materials, such as growth factors and other agents useful for tissue regeneration. Tissue scaffolds may be used in vivo or in vitro.

Typically tissue scaffolds are formed in vitro. In order for a scaffold produced in vitro to be used in vivo it must be implanted into a patient, this is normally done using an invasive surgical procedure. The procedure requires an incision to be made into a tissue which is large enough to allow the insertion of the prefabricated scaffold. In order to perform this method the surgeon must know the size and shape of the volume to be filled by the scaffold before the implantation.

An aim, of the present invention is to provide a scaffold composition which can be delivered without the need for invasive surgery.

According to a first aspect, the invention provides a composition comprising polymer particles and a carrier, wherein the polymer particles are a mixture of at least a first polymer and a second polymer, wherein the first polymer is at least partially soluble or dispersible in the carrier, and wherein the polymer particles are arranged such that they can join together to form a scaffold of polymer particles, and wherein the composition is administrable to a human or non-human animal.

Preferably, the composition is administrable to a human or non-human animal prior to the joining together of polymer particles to form a scaffold of polymer particles.

The joining together of the polymer particles to form a scaffold may be viewed as a "solidification" of these particles to form the scaffold.

In particular, preferably the scaffold formed by the composition of the invention is a solid structure, and formation of the scaffold from the particles in the composition may be referred to as solidification.

Preferably when a composition solidifies to form a scaffold it changes from a suspension or deformable viscous state to a solid state in which the scaffold formed is self-supporting and retains its shape. The solid scaffold formed may be brittle.

The joining together of the polymer particles may be due to, for example, one or more of fusion, adhesion, cohesion and entanglement of the polymer and/or particles.

In one embodiment, the invention provides a composition polymer particles and a carrier, wherein the polymer particles are a mixture of at least a first polymer and a second polymer, wherein the first polymer is at least partially soluble or dispersible in the carrier, and wherein the polymer particles are arranged to join to form a scaffold of polymer particles after the composition is administered to a human or non-human animal.

Preferably, the polymer particles are a mixture of a first polymer together with a second polymer, wherein the mixture of the two polymers has a glass transition temperature lower than the glass transition temperature of the second type of polymer on its own.

Preferably, the polymer particles are a mixture of a first polymer together with a second polymer, wherein the mixture of the two polymers has a glass transition temperature of 45° C. or less and wherein this glass transition temperature of the mixture of the two polymers is lower than the glass transition temperature of the second type of polymer on its own.

Preferably, the polymer particles are a mixture of a first polymer together with a second polymer, wherein the mixture of the two polymers has a glass transition temperature of 40° C. or less and wherein this glass transition temperature of the mixture of the two polymers is lower than the glass transition temperature of the second type of polymer on its own.

Preferably, the polymer particles are a mixture of a first polymer together with a second polymer, wherein the mixture of the two polymers has a glass transition temperature of 37° C. or less and wherein this glass transition temperature of the mixture of the two polymers is lower than the glass transition temperature of the second type of polymer on its own.

Preferably, the polymer particles are a mixture of a first polymer together with a second polymer, wherein the mixture of the two polymers has a glass transition temperature of below 37° C. but wherein the second type of polymer on its own has a glass transition temperature of above 37° C.

Preferably, the first polymer is sufficiently soluble or dispersible in the carrier that the first polymer will at least partially leach into the carrier. For example, the first polymer may be sufficiently soluble or dispersible in the carrier that the first polymer will at least partially leach into the carrier within 20 hours or less, such as 10 hours or less, preferably 5 hours or less, such as 2 hours or less, e.g. 1 hour or less. In one embodiment, the first polymer may be sufficiently soluble or dispersible in the carrier that 1 wt % or more of the first polymer, such as 5 wt % or more, e.g. 10 wt % or more, such as 25 wt % or more, will partially leach into the carrier within 20 hours or less, such as 10 hours or less, preferably 5 hours or less, such as 2 hours or less, e.g. 1 hour or less.

Preferably, the first polymer is a plasticiser. In one embodiment, the plasticiser is selected from one or more of: polyethylene glycol (PEG), poly(propylene adipate) (PPA), poly(butylene adipate) (PBA), poly lactic acid (PLA), polyglycolic acids (PGA), poly(D,L-lactide-co-glycolide) (PLGA), poly propylene glycol, poly caprolactone, polyethylene glycol polypropylene block co-polymers, for example that sold under the trade mark Pluronics™, and low molecular weight oligomers of any of the preceding polymers (e.g. an oligomer having a molecular weight of 20 kDa or less). The plasticiser may also be selected from conventional plasticisers including but not limited to adipates, phosphates, phthalates, sebacates, azolates and citrates.

In particular, the polymer particles may be a mixture of polymers, wherein the first polymer is PEG.

The PEG may have any suitable molecular weight. Preferably, the PEG has a molecular weight of 800 or less, such as 600 or less, more preferably 400 or less. Such polymers may result in the formation of scaffolds with improved compressive strength. In a preferred embodiment, PEG300 is used. In another preferred embodiment, PEG400 is used.

Preferably, the first polymer causes chain mobilization in the second polymer, lowering the glass transition temperature and hence causing the material to soften at lower temperatures than would otherwise be possible.

Preferably, the amount of the first polymer present in the polymer particles is from 1 to 20% by weight, e.g. from 1 to 15% by weight, such as from 2 to 12% by weight, more preferably from 3 to 10% by weight, such as from 4 to 8% by weight, e.g. from 5 to 7% by weight.

Preferably, the second polymer is an amorphous or semi crystalline polymer. Preferably the second polymer comprises one or more polymer selected from the group comprising poly(D,L-lactide-co-glycolide)(PLGA), poly D,L-lactic acid (PDLLA), polyethylene glycol (PEG), polyethyleneimine (PEI), poly($\alpha$-hydroxyacids), polylactic or polyglcolic acids, poly-lactide poly-glycolide copolymers, poly-lactide poly-glycolide polyethylene glycol copolymers, polyesters, poly($\epsilon$-caprolactone), poly(3-hydroxybutyrate), poly(s-caprioc acid), poly(p-dioxanone), poly (propylene fumarate), poly(ortho esters), polyol/diketene acetals addition polymers, polyanhydrides, poly(sebacic anhydride) (PSA), poly(carboxybiscarboxyphenoxyphosphazene) (PCPP), poly [bis(p-carboxyphenoxy) methane] (PCPM), copolymers of SA, CPP and CPM (as described in Tamat and Langer in Journal of Biomaterials Science Polymer Edition, 3, 315-353. 1992 and by Domb in Chapter 8 of The Handbook of Biodegradable Polymers, Editors Domb A J and Wiseman R M, Harwood Academic Publishers), poly(amino acids), poly(pseudo amino acids), polyphosphazenes, derivatives of poly[(dichloro) phosphazene], poly [(organo) phosphazenes], polyphosphates, polyethylene glycol polypropylene block co-polymers for example that sold under the trade mark Pluronics™, natural or synthetic polymers such as silk, elastin, chitin, chitosan, fibrin, fibrinogen, polysaccharides (including pectins), alginates, collagen, peptides, polypeptides or proteins, copolymers prepared from the monomers of any of these polymers, random blends of these polymers, any suitable polymer and mixtures or combinations thereof.

Preferably the second polymer is selected from the group comprising poly lactic acid (PLA), polyglycolic acids (PGA), poly(D,L-lactide-co-glycolide)(PLGA), poly D, L-lactic acid (PDLLA), poly-lactide poly-glycolide copolymers and combinations thereof.

In a particularly preferred embodiment, the first polymer is PEG and the second polymer is selected from the group comprising poly lactic acid (PLA), polyglycolic acids, poly (D,L-lactide-co-glycolide)(PLGA), poly D, L-lactic acid (PDLLA), poly-lactide poly-glycolide copolymers and combinations thereof.

In one preferred embodiment, the first polymer is PEG and the second polymer is PLGA.

Preferably, the composition comprises a mixture of a first polymer which is a plasticiser together with a second polymer, wherein the mixture of the two polymers has a glass transition temperature lower than the glass transition temperature of the second type of polymer on its own.

Preferably, the composition comprises a mixture of a first type of polymer which is a plasticiser together with a second type of polymer, wherein the mixture of the two types of polymer has a glass transition temperature of below 37° C. but wherein the second type of polymer has a glass transition temperature of above 37° C.

The carrier is preferably an aqueous carrier, in particular water or an aqueous solution or suspension, such as saline, plasma, bone marrow aspirate, buffers, such as Hank's Buffered Salt Solution (HBSS), HEPES (4-(2-hydroxyethyl)-1-piperazineethanesulfonic acid), Ringers buffer, Krebs buffer, Dulbecco's PBS, and normal PBS; simulated body fluids, plasma platelet concentrate and tissue culture medium.

The carrier may, optionally, contain one or more suspending agent. The suspending agent may be selected from carboxy methylcellulose (CMC), mannitol, polysorbate, poly propylene glycol, poly ethylene glycol, gelatine, albumin, alginate, hydroxyl propyl methyl cellulose (HPMC), hydroxyl ethyl methyl cellulose (HEMC), bentonite, tragacanth, dextrin, sesame oil, almond oil, sucrose, acacia gum and xanthan gum and combinations thereof.

The ratio of polymer to carrier may be from 4:1 to 1:4, e.g. from 3:1 to 1:3, such as from 2:1 to 1:2, preferably from 1.5:1 to 1:1.5, e.g. from 1.25:1 to 1:1.25, such as about 1:1.

By using a composition which solidifies to form a scaffold after administration a scaffold can be formed which conforms to the shape of where it is placed, for example, the shape of a tissue cavity into which it is placed. This overcomes a problem with scaffolds fabricated prior to administration which must be fabricated to a specific shape ahead of administration, and cannot be inserted through a bottle-neck in a cavity and cannot expand to fill a cavity.

Preferably, the polymer particles are raised close to or above their onset temperature on injection into the body, and hence the polymer particles will cross-link to one or more other polymer particles to form a scaffold or matrix. By cross-link it is meant that adjacent polymer particles become joined together. For example, the particles may cross-link due to entanglement of the polymer chains at the surface of one particle with polymer chains at the surface of another particle. There may be adhesion, cohesion or fusion between adjacent particles.

The first polymer is sufficiently soluble/dispersible in the carrier such that it will at least partially leach into the carrier, leaving behind the second polymer. Preferably, humid conditions are used which encourage the leaching of the first polymer into the carrier. As carrier dissipates in the body, ongoing leaching of the first polymer into residual carrier or body fluids may occur.

The second type of polymer particle on its own preferably has a higher glass transition temperature than the mixture of the two types of polymer particle. Accordingly, following leaching of the first polymer, the polymer particles harden and fusion points with neighbouring particles may become tough. Therefore a hardened scaffold structure is formed.

Accordingly, a scaffold having improved hardness and strength may be formed, for example a scaffold having improved compressive strength.

In one embodiment as well as the composition comprising polymer particles which are a mixture of the two polymers, the composition may additionally comprise further polymer particles. Such further polymer particles may comprise any polymer, for example any of the polymers mentioned above in relation to the first and second polymers, for example PLA, PGA or PLGA. These further polymer particles may comprise a polymer that is the same as the one of the polymers in the polymer particles which are a mixture of two polymers.

Preferably the term administered refers to the placing of a composition according to the invention in or on the body of a human or non-human animal.

Preferably the composition is intended to be administered by injection into the body of a human or non-human animal. If the composition is injected then the need for invasive surgery to position the scaffold is removed.

Preferably the composition is sufficiently viscous to allow administration of the composition to a human or non-human animal, preferably by injection. Preferably the composition is intended to be administered at room temperature, and is preferably viscous at room temperature. The term room temperature is intended to refer to a temperature of from about 15° C. to about 25° C., such as from about 20° C. to about 25° C.

Alternatively, the composition may be heated to above room temperature, for example to body temperature (about 37° C.) or above, for administration. The composition is preferably flowable or viscous at this temperature in order to aid its administration to a human or non-human animal.

Preferably the composition has a viscosity which allows it to be administered, using normal pressure, from a syringe which has an orifice of about 4 mm or less. The size of the orifice will depend on the medical application, for example, for many bone applications a syringe with an orifice of between about 2 mm and about 4 mm will be used, however, for other applications small orifices may be preferred. Preferably "normal pressure" is that applied by a human administering the composition to a patient using one hand.

Preferably the composition is of sufficient viscosity such that when it is administered it does not immediately dissipate, as water would, but instead takes the form of the site where it is administered. Preferably some of the carrier will dissipate over time.

Preferably the polymer particles are suspended in the carrier. In one embodiment, if the composition is left to stand substantially all the polymer particles will remain suspended in the carrier, and will not fall out of suspension. Alternatively, the composition may be such that if the composition is left to stand some or all the polymer particles will fall out of suspension.

Preferably the polymer particles themselves are not readily soluble in the carrier, e.g. it may be that not all of the polymer particles would dissolve in the carrier at 25° C. after one hour. For example, some or all of the polymer particles may be insoluble in the carrier.

However, the first polymer is at least partially soluble/dispersible in the carrier. Preferably the polymer particles comprise a mixture of plasticiser and another polymer, and the plasticiser is soluble/dispersible in the carrier.

The carrier may interact with the polymer particles. The carrier may interact with the polymer particles to prevent or slow the formation of a scaffold and to allow the polymer particles to be administered to a human or non-human animal before a scaffold forms. The carrier may prevent interaction between the polymer particles due to separation of the particles by suspension in the carrier. It may be that the carrier completely prevents the formation of the scaffold prior to administration, or it may simply slow the formation, e.g. permitting the scaffold to begin but not complete formation prior to administration. In one embodiment the composition comprises sufficient carrier to prevent the formation of a scaffold even when the composition is at a temperature which, in the absence of the carrier, would cause the polymer particles to form a scaffold. In one embodiment, the composition comprises sufficient carrier to slow the formation of a scaffold such that when the composition is at a temperature which, in the absence of the carrier, would cause the polymer particles to readily form a scaffold, a scaffold does not readily form, e.g. does not form over a timescale such as one hour to five hours.

The carrier may interact with the polymer particles and cause the surface of the particles to swell, whilst remaining as discrete particles, thus allowing administration by injection. However, once the composition has been administered and the carrier begins to dissipate the particles may begin to de-swell. De-swelling may assist the joining together of particles.

Interaction of the polymer particles with the carrier may cause the glass transition temperature of the polymer particles to change. For example, the interaction may cause the glass transition temperature to be lowered.

The carrier may act as a lubricant to allow the polymer particles to be administered to a human or non-human animal, preferably by injection. Preferably the carrier provides lubrication when the composition is dispensed from a syringe. The carrier may help to reduce or prevent shear damage to particles dispensed from a syringe.

In one embodiment, the composition comprising the polymer particles and the carrier remains viscous even at temperatures above the glass transition temperature of the polymer particles.

In one embodiment, the composition is intended to be administered at a temperature above the glass transition temperature of the polymer particles. For example, the composition may be intended to be administered at a temperature of up to about 10° C., 20° C., 30° C. or 40° C. above the glass transition temperature of the polymer particles.

In one embodiment, the composition, before administration to a human or animal, comprises sufficient carrier to prevent the polymer particles from forming a scaffold even when the composition is at temperature equal to or above the glass transition temperature of the polymer.

Preferably the glass transition temperature of the polymer particles is above room temperature.

In one embodiment, the composition is sufficiently viscous that when administered the particles remain substantially where they are injected, and do not immediately dissipate. Preferably, the scaffold forms before there has been any substantial dissipation of the particles. Preferably more than about 50%, 60% 70%, 80% or 90% of the particles injected into a particular site will remain at the site and form a scaffold at that site.

In one embodiment, when the composition of the invention is administered to a human or non-human animal at least some of the carrier dissipates away from the polymer particles. In one embodiment the carrier dissipates into the water/plasma phase within the body. In one embodiment at least about 20%, 30%, 40%, 50%, 60%, 70%, 80% or 90% or more of the carrier dissipates from the composition after it is administered to a human or non-human animal. In one embodiment, at least 95% of the carrier, that is substantially all of the carrier, dissipates from the composition when it is placed in a human or non-human animal body. Accordingly, it will be understood that, the solidified scaffold composition may contain little or no carrier. In one embodiment any carrier remaining in the scaffold will be located in pores in the scaffold, and is not integral to the scaffold, and will in time be replaced by body fluid or cells.

In one embodiment the polymer particles will form a scaffold in the human or non-human animal once at least some of the carrier has dissipated away from the polymer particles.

Preferably, in order for the polymer particles to form a scaffold the temperature around the particles, for example in the human or non-human animal where the composition is administered, must be approximately equal to, or greater than, the glass transition temperature of the polymer particles. Preferably, at such temperatures the polymer particles will cross-link to one or more other polymer particles to form a scaffold or matrix. By cross-link it is meant that adjacent polymer particles become joined together. For example, the particles may cross-link due to entanglement of the polymer chains at the surface of one particle with polymer chains at the surface of another particle. There may be adhesion, cohesion or fusion between adjacent particles.

The particles in the composition may be adapted to cross-link once administered to a human or non-human animal. Preferably cross-linking occurs at a temperature above the glass transition temperature of the polymer particles. In one embodiment, cross-linking occurs when at least some of the carrier has dissipated from the composition. The cross-linking of polymer particles may cause the polymer particles to form a scaffold.

In one embodiment, in order for the particles in the composition to cross-link and form a scaffold the temperature of the particles must be at or above the glass transition temperature of the particles, and at least some of the carrier must have dissipated from the composition.

Preferably a scaffold would form in a human or non-human animal body after the composition has been administered and at least some of the carrier has dissipated.

The particles may be arranged to be cross-linked using a linker molecule. The method of cross-linking used may be as described in PCT/GB2004/001419.

Preferably the polymer particles are such that in the absence of any carrier they would form a scaffold/matrix when placed at a temperature equal to or above their glass transition temperature. At or above the glass transition temperature the polymer particles may cross-link to form a scaffold/matrix.

A viscous composition according to the invention may be used as an injectable scaffold. In order to be used as an injectable scaffold the composition must be sufficiently viscous that it can be administered, preferably by injection, to a human or non-human animal subject, where it will then solidify to form a scaffold. The scaffold may be used as a platform for tissue growth. The scaffold may provide a support for tissue formation. The composition may be used alone, or it may be seeded with a cellular therapy/cells or co-administered with a cellular therapy/cells.

Cellular therapy involves using cells to repair tissues that have been damaged, for example by disease, to generate new tissues with desired functional activities.

Preferably the scaffold formed following injection of the composition is suitable for efficient tissue repair in vivo.

The scaffold formed may be porous, that is, it may have pores or spaces between the particles. The pores may arise due to the packing properties of the polymer particles, for example, if the particles are irregular or spherical in shape then pores will form between the particles.

The polymer particles may also be referred to as polymer microparticles, and the terms particle(s) and microparticle(s) are used interchangeably. The particles may be porous or solid, or a mixture thereof. The particles may be substantially spherical, in which case they may be referred to as microspheres.

Preferably the polymer particles have a size in their longest dimension, or their diameter if they are substantially spherical, of less than about 3000 µm and preferably more than about 1 µm. More preferably the particles have a size in their longest dimension, or their diameter, of less than about 1000 µm. Preferably the particles have a size in their longest dimension, or their diameter, of between about 50 µm and about 500 µm, more preferably between about 200 µm and about 500 µm. Preferably polymer particles of the desired size are unable to pass through a sieve or filter with a pore size of about 50 µm, but will pass through a sieve or filter with a pore size of about 500 µm. More preferably polymer particles of the desired size are unable to pass through a sieve or filter with a pore size of about 200 µm, but will pass through a sieve or filter with a pore size of about 500 µm.

The polymers used may be biodegradable and/or biocompatible.

Preferably the scaffold produced by the composition of the invention is biocompatible and/or biodegradable.

Formation of the scaffold from the composition, once administered to a human or non-human animal, preferably takes from about 20 seconds to about 24 hours, preferably between about 1 minute and about 5 hours, preferably between about 1 minute and about 1 hour, preferably less than about 30 minutes, preferably less than about 20 minutes. Preferably the solidification occurs in between about 1 minute and about 20 minutes from administration.

The carrier may be biodegradable and/or biocompatible and/or bio-absorbable.

Preferably the composition comprises from about 30% to about 70% particles and from about 30% to about 70% carrier; e.g. the composition may comprise from about 40% to about 60% particles and from about 40% to about 60% carrier; the composition may comprise about 50% particles and about 50% carrier. The aforementioned percentages all refer to percentage by weight.

Changing the atmosphere/environment around the viscous composition may cause the polymer particles to solidify.

Preferably the composition can be stored at room temperature, pressure and atmosphere until needed. This has the advantage that storage is cheap and easy, and administration is straightforward. Alternatively, the composition may be stored in a fridge or freezer before use. It may be that the particles of the composition are stored in a dry form, and the carrier is only added when the composition is needed for use.

Other substances such as growth factors and/or adhesion molecules may be incorporated into the particles and/or carrier before and/or after they are combined to form the composition of the invention. Other substances incorporated into the particles and/or carrier may be selected from the group comprising amino acids, peptides, proteins, sugars, antibodies, nucleic acid, antibiotics, antimycotics, growth factors, steroids, synthetic material, adhesion molecules, colourants/dyes (which may be used for identification), radioisotopes (which may be for X-ray detection and/or monitoring of degradation), and other suitable constituents, or combinations thereof.

The composition may also include cells, the cells may be incorporated into the composition before or after the carrier and particles are mixed to form the composition. The cells may be derived from a patient to be treated with the composition. The cells may include chondrocytes, chondroblasts, osteocytes, osteoblasts, fibroblasts, stem cells and any other suitable cells.

Products may be delivered between or from within the particles by incorporating such products into the particles and/or carrier before and/or after they are combined to form the composition of the invention. For example, inorganic materials, ceramics, growth factors, proteins, and/or small molecules may be delivered between or from within the particles by incorporating such products into the particles and/or carrier before and/or after they are combined to form the composition of the invention.

The composition may comprise a mixture of temperature sensitive particles and non-temperature sensitive particles. Preferably non-temperature sensitive particles are particles with a glass transition temperature which is above the temperature at which the composition is intended to be used. Preferably, in a composition comprising a mixture of temperature sensitive particles and non-temperature sensitive particles the ratio of temperature sensitive to non-temperature sensitive particles is about 3:1, or lower, for example, 4:3. The temperature sensitive particles are preferably capable of crosslinking to each other when the temperature of the composition is raised to or above the glass transition a temperature of these particles. By controlling the ratio of temperature sensitive particles to non-temperature sensitive particles it may be possible to manipulate the porosity of the resulting scaffold.

Preferably the composition does not react with the plastic used to make syringes.

Particles for use in the invention may be made by a method comprising the steps of:
  mixing a first polymer with a second polymer to form a polymer mixture, wherein the first and/or second polymers are molten;
  solidifying the polymer mixture to provide a solid polymer mixture;
  breaking-up the solid polymer mixture to produce solid microparticles.

The mixing of the first and second polymers may be achieved by blending. The first and/or second polymer may be melted to be molten prior to or during mixing of the first and second polymers. The mixing may be conducted on a hot plate.

The polymer mixture may be solidified by cooling the mixture; the mixture may be cooled to room temperature or lower.

The solid polymer mixture may be broken-up into particles, for use in the composition, by using grinding, grating, pulverising, milling, hammering, crushing, spheronisation, or combinations thereof.

Alternatively, methods selected from emulsion methods (including single and double emulsion), phase inversion, solvent extraction, solvent evaporation, hot melt or solvent spraying, membrane emulsification, precipitation emulsification, supercritical fluids, sonication, microfluidic droplet generation, non aqueous emulsion methods, granulation, and combinations thereof may be used to prepare particles for use in the invention.

In one embodiment the composition does not comprise a cement. In one embodiment the composition does not comprise a calcium phosphate cement, a ceramic cement or a PMMA bone cement.

In one embodiment, the composition may comprise one or more further particulate material. Preferably, the further particulate material does not join together with the polymer particles to actually form the scaffold. However, it may be present in the formed scaffold due to being either dispersed or encapsulated within the particles or caught up in the structure. Preferably, the further particulate material is a ceramic. For example, the further particulate material may be a calcium phosphate particulate material, such as beta tricalcium phosphate or hydroxyapatite, or it may be bioglass. The further particulate material may be present in the composition in an amount of from 0 to 90% by weight; preferably from 5 to 60% by weight; more preferably from 10 to 50% by weight, e.g. from 15 to 45% by weight, such as from 20 to 40% by weight.

In one embodiment, ceramic particles may additionally be present in the composition. This will typically be a temperature insensitive particle type. Alternatively or additionally, polymer particles in the composition may themselves contain a ceramic component. This will typically be a temperature insensitive particle type.

The inclusion of ceramic material either as separate particles or within the polymer particles may enhance osteoconductivity and/or add osteoinductivity.

According to another aspect, the invention provides a method of providing a scaffold in a tissue of a human or animal body comprising injecting a composition according to the first aspect of the invention into the tissue, and allowing the polymer particles to join together to form a solid scaffold.

The method may be practised on tissue in vivo or in vitro.

In one embodiment, the method is carried out in humid conditions. Such conditions may encourage the leaching of the first polymer into the carrier. Accordingly, a scaffold having improved hardness and strength may be formed, for example a scaffold having improved compressive strength.

Conditions of 30% or higher relative humidity may be used, such as 40% or higher, e.g. 50% or higher, such as 60% or higher, for example 70% or higher.

The method may be used in cosmetic applications, e.g. to provide a scaffold in wrinkle tissue to reduce the appearance of the wrinkle.

According to a further aspect, the invention provides a scaffold produced by providing a composition according to the first aspect of the invention and causing the polymer particles to join together to form a solid scaffold.

According to a yet further aspect, the invention provides a scaffold produced by any method of the invention.

According to another aspect, the invention provides an injectable scaffold material comprising a composition according to the first aspect of the invention.

According to a further aspect, the invention provides the use of composition according to the first aspect of the invention in the manufacture of a medicament for use in the production of a tissue scaffold.

The scaffold formed by any method and/or composition of the invention may be used to treat damaged tissue. In particular, the scaffold may be used to encourage or allow cells to re-grow in a damaged tissue.

The composition of the invention may be used to produce scaffolds for use in the treatment of a disease or medical condition, such as, but not limited to, Alzheimer's disease, Parkinson's disease, osteoarthritis, burns, spinal disk atrophy, cancers, hepatic atrophy and other liver disorders, bone cavity filling, regeneration or repair of bone fractures, diabetes mellitus, ureter or bladder reconstruction, prolapse of the bladder or the uterus, IVF treatment, muscle wasting disorders, atrophy of the kidney, organ reconstruction and cosmetic surgery.

According to a further aspect, the invention provides the use of a composition according to the invention as an injectable scaffold material in tissue regeneration and/or in the treatment of tissue damage.

According to a yet further aspect, the invention provides the use of a composition according to the invention in the preparation of a scaffold for the culturing of cells. The scaffold and cultured cells may be used for metabolite processing, drug testing or protein secretion. The cultured cells may be stem cells, liver cells or any other suitable cells.

According to another aspect, the invention provides a kit for use in producing a tissue scaffold comprising a composition according to the invention and instructions to use the composition.

The kit may include a syringe for use in injecting the composition. The composition may be provided preloaded in the syringe, ready for use.

Preferably the kit can be stored either refrigerated or at room temperature.

According to another aspect, the invention provides a method of producing a scaffold, comprising:
(a) providing a composition comprising polymer particles and a carrier, wherein the polymer particles are a mixture of a first polymer together with a second polymer, wherein the mixture of the two polymers has a glass transition temperature lower than the glass transition temperature of the second type of polymer on its own, and wherein the first polymer is at least partially soluble or dispersible in the carrier, and wherein the polymer particles are arranged such that they can join together to form a scaffold of polymer particles,
(b) allowing the polymer particles to join together to form a solid scaffold, and
(c) allowing the first polymer to leach into the carrier, such that the glass transition temperature increases and the scaffold hardens.

Preferably, the leaching of first polymer into the carrier in step (c) results in an increase in the compressive strength of the scaffold obtained in step (b).

Humid conditions may be used in step (c) to encourage leaching of the first polymer.

The skilled man will appreciate that the preferred features of the first aspect of the invention can be applied to all aspects of the invention.

Embodiments of the invention will now be described, by way of example only, with reference to the following figures.

EXAMPLE 1—PRODUCTION AND TESTING OF SCAFFOLDS a) Scaffold Production

Microparticles fabricated from poly(lactic-co-glycolic acid) and the plasticizing agent poly(ethylene glycol) (5%) were combined with a saline solution (0.9%) in a 1:1 ratio and the mixture extruded from a syringe into a plastic sealable bag pre-heated to 37° C. The bag was sealed and placed in an oven for 2 hours to form scaffolds, before removal of the scaffold and analysis. The bag mimicked the in vivo environment by retaining moisture resulting in a more humid environment. The experiment was repeated but without using the bag, thus acting as a control (non-humid environment).

b) Rheological Assessment of Particles

Scaffolds fabricated as in part a) were broken up into particulate form and dried overnight, prior to rheological assessment. The thermal profile of both particulate materials (humid and non-humid) along with naked PLGA was assessed with a rheometer (Anton Parr Physica—MCR 301) using a parallel plates geometry. The samples (0.5 g) were assessed by using an oscillation test (0.1% strain) to measure the change in phase angle (tan delta) as the material was heated from 4° C. to 90° C.

Figure 1:
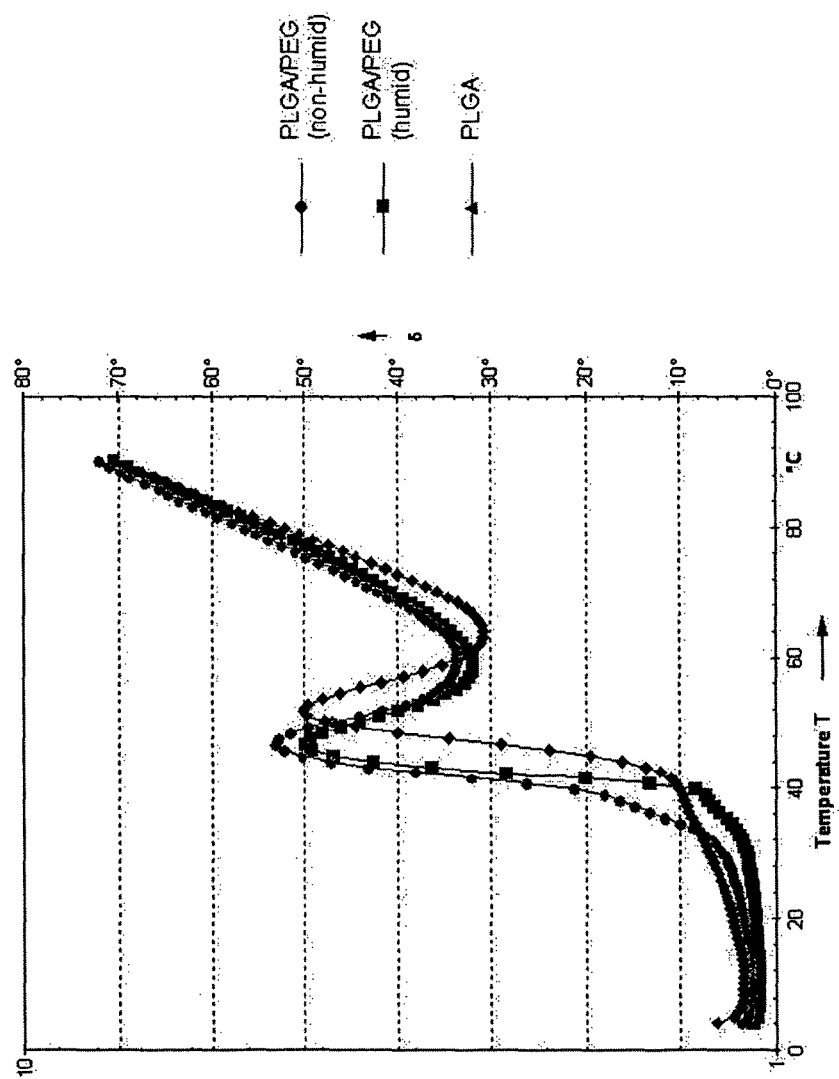
FIG. 1 illustrates the rheological profiles of PLGA/PEG scaffolds after fabrication in (a) humid conditions where PEG leaches out of the polymer particles and (b) non-humid conditions where PEG does not leach out of the polymer particles.

The results of the rheological assessment are shown in FIG. 1.

c) Mechanical Testing of Scaffolds

Scaffolds were prepared in humid and non-humid conditions as in part a). A texture analyzer (Stable Micro Systems TX.HD plus was used to assess the relative compressive strength of scaffolds fabricated in both the humid and non-humid conditions. A load of 50 kg was applied to each scaffold at a cross head speed of 1 mm/sec using a 10 mm diameter probe at room temperature. The compressive yield strength was recorded in megapascals (MPa) for each scaffold using a plot of stress Vs strain by taking the first fracture peak as the yield point.

Figure 2:
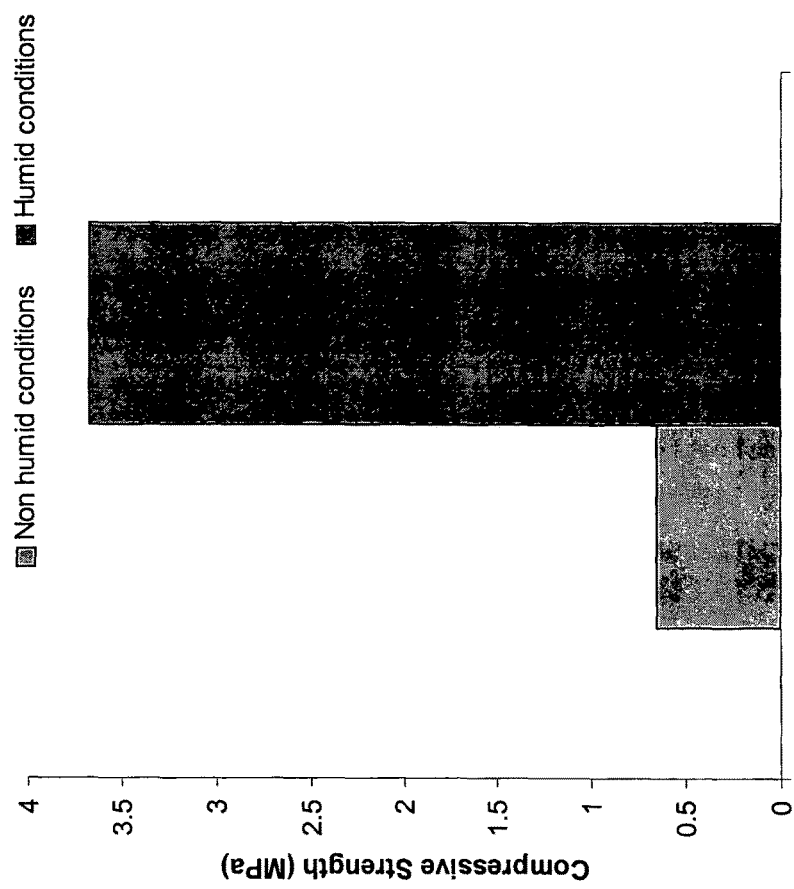
FIG. 2 illustrates the relative compressive strengths of PLGA/PEG scaffolds after fabrication in both humid and non-humid conditions.

The results of the compressive strength testing are shown in FIG. 2.

EXAMPLE 2—PEG LEACHING QUANTIFICATION a) Sample Preparation

PLGA scaffolds prepared in non-humid conditions (n=3) and containing 5% PEG were suspended in distilled water (1 ml per scaffold) and kept in an incubator at 37° C./5% $CO_2$. At specific time points the water was aspirated from the scaffolds, stored at 4° C. for subsequent analysis and replaced with fresh. The time points used were as follows: 30 min, 1 hr, 2 hrs, 4 hrs, 8 hrs, 24 hrs, 48 hrs, 72 hrs, 96 hrs, 7 days, 10 days, 14 days.

Each 1 ml aliquot was analyzed using mass spectrometry (MS) to assess the concentration of PEG in each and thus the quantity of PEG remaining in the scaffold at each time point. A calibration curve was prepared using known concentrations of PEG in distilled water with a further 1 in 1000 dilution required for each sample due to the sensitivity of the MS instrument.

b) Mass Spectrometry

Mass spectrometry (MS) on the known and unknown PEG concentrations was carried out using a Waters Quattro Ultima mass spectrometer (Agilent 1100 system with a binary pump and degasser). The samples were monitored for one minute in SIR (selected ion recording) mode to detect PEG 400 ions with the following masses: 300.2, 413.2 and 613.2 Da (with a span of 0.01Th each at a cone voltage of 35V). Cone gas was set at 70 l/hr and desolvation at 520 l/hr. The source temperature was 125° C. and the desolvation temperature was 350° C.

A carrier solution of 20% water, 80% Acetonitrile and 0.1% formic acid was used to introduce the PEG samples into the MS. The following flow profile was used to ensure smooth peak shape and efficient removal of sample from the system: 200 µl/min between 0-0.2 minutes increasing to 500 µl/min at 0.2 minutes and maintained at 500 µl/min for 0.8 minutes.

Figure 3A:
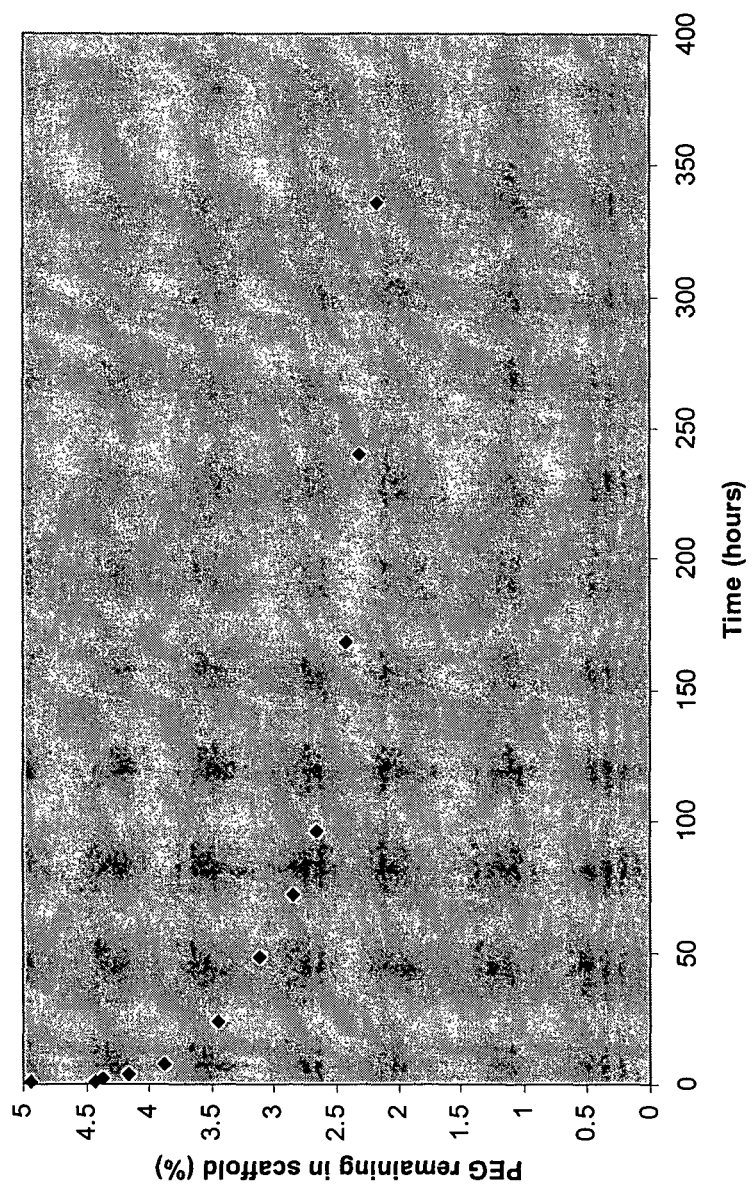
FIG. 3a is a mass spectra showing the leaching of PEG from the scaffold, which shows the quantity of PEG remaining in the scaffold at each time point, in relation to PEG 400 ions with mass of 300.2 Da.
Figure 3B:
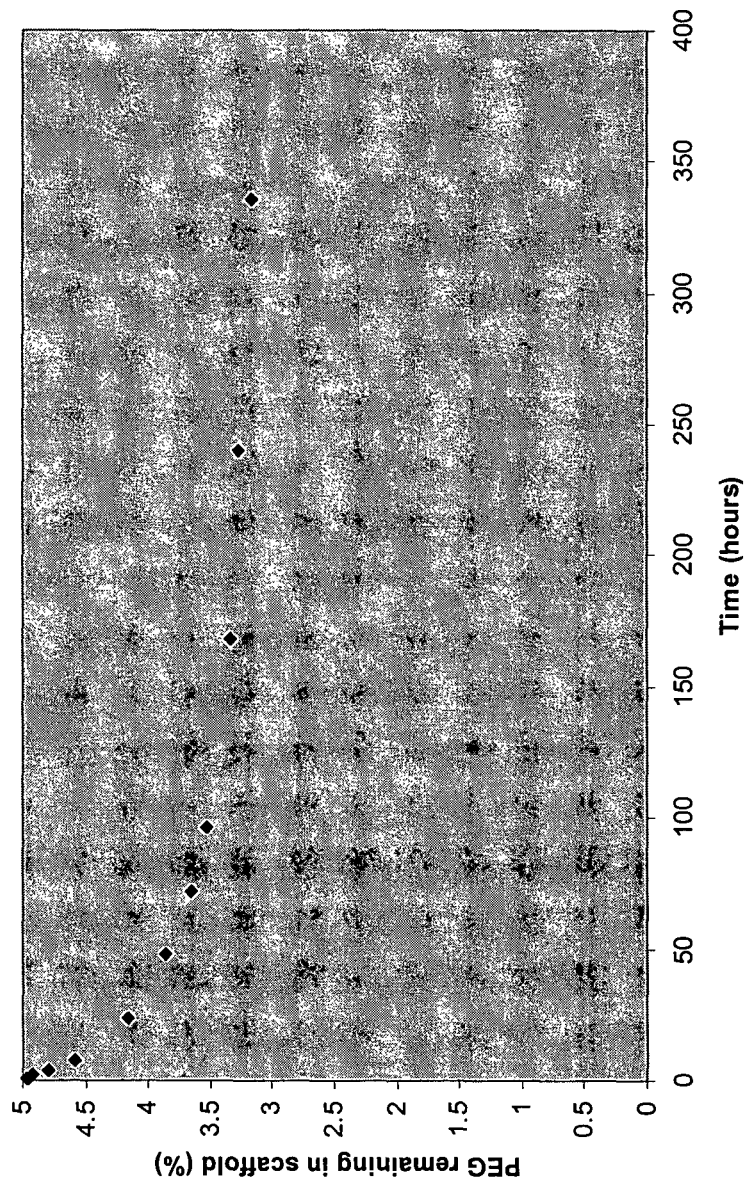
FIG. 3b is a mass spectra showing the leaching of PEG from the scaffold, which shows the quantity of PEG remaining in the scaffold at each time point, in relation to PEG 400 ions with mass of 413.2 Da.
Figure 3C:
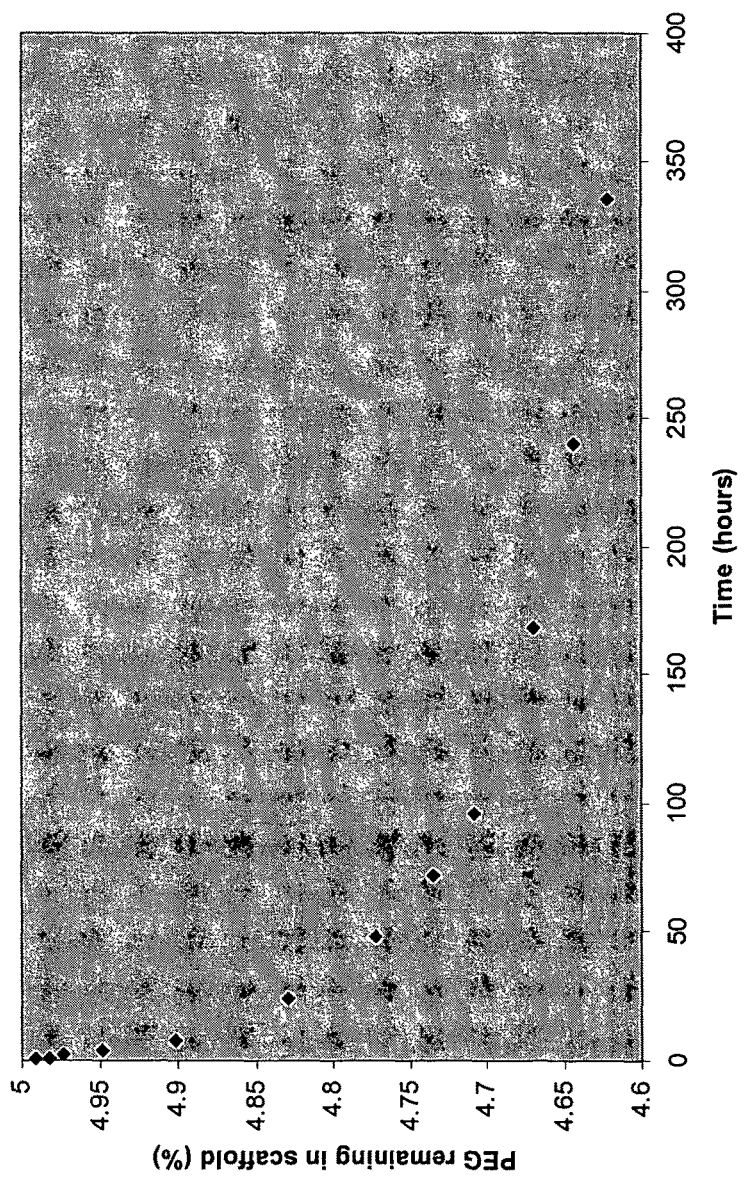
FIG. 3c is a mass spectra showing the leaching of PEG from the scaffold, which shows the quantity of PEG remaining in the scaffold at each time point, in relation to PEG 400 ions with mass of 613.2 Da.

The mass spectra are shown in FIGS. 3a to 3c.

Conclusions

When comparing the rheological profile of the PLGA/PEG scaffold kept in dry conditions with that kept in humid conditions there is a shift to the left between 20 and 40° C., indicating additional leaching of PEG from the PLGA material under humid conditions.

This additional leaching of the PEG is considered to be a contributing factor for the increased compressive strength of the scaffold produced in humid conditions when compared to that fabricated in non-humid conditions.

Data from the MS shows that the majority of the PEG released does so within the first 24-48 hours (burst release). This burst release is characteristic of porous scaffolds whereby the pores act as channels through which the PEG trapped at the surface of the scaffolds can diffuse out into the surrounding water. The rate of PEG leaching is dependent upon mass with the 302.2 spectra demonstrating the most rapid release and the 613.2 spectra demonstrating the slowest release. Crucially, both the 302.2 and 413.2 spectra confirm that PEG is leaching out of the material in the short time frames (0-2 hours) that were used to fabricate the scaffolds in humid conditions.

EXAMPLE 3—EFFECT OF MOLECULAR WEIGHT OF PEG a) Scaffold Fabrication

Three molecular weights of PEG were used; PEG 200, 300 and 400. Nine scaffolds were fabricated to give n=3 for all three formulations.

A blend of PLGA (35 KDa) and PEG (10% loading) was created with each of the three PEG molecular weights using the melt blending method.

The blended material was ground into microparticles, which were then sieved into a 200-350 µm size fraction. To fabricate each scaffold, 300 mg of each PLGA/PEG blend for each formulation was combined with 0.35 cc of saline. The material was packed into a PTFE mould (12 mm×6 mm) and sintered for 2 hours at 37° C.

After fabrication, the scaffolds were retained in the moulds (but with the bases removed) removed from the plastic bags and submerged in 30 ml of distilled water inside a 100 ml plastic container. The containers were sealed and retained in the oven for a further 24 hours at 37° C.

b) Mechanical Testing

Compressive testing was carried out using a TA.HD+ texture analyzer (stable micro systems) to determine the force required to fracture each scaffold at increasing strain.

Each scaffold was compressed with a 50 kg load at a crosshead speed of 0.04 mm per/sec using a 10 mm diameter delrin probe to apply the force. All testing was carried out at 37° C. using a temperature controlled chamber.

Figure 4:
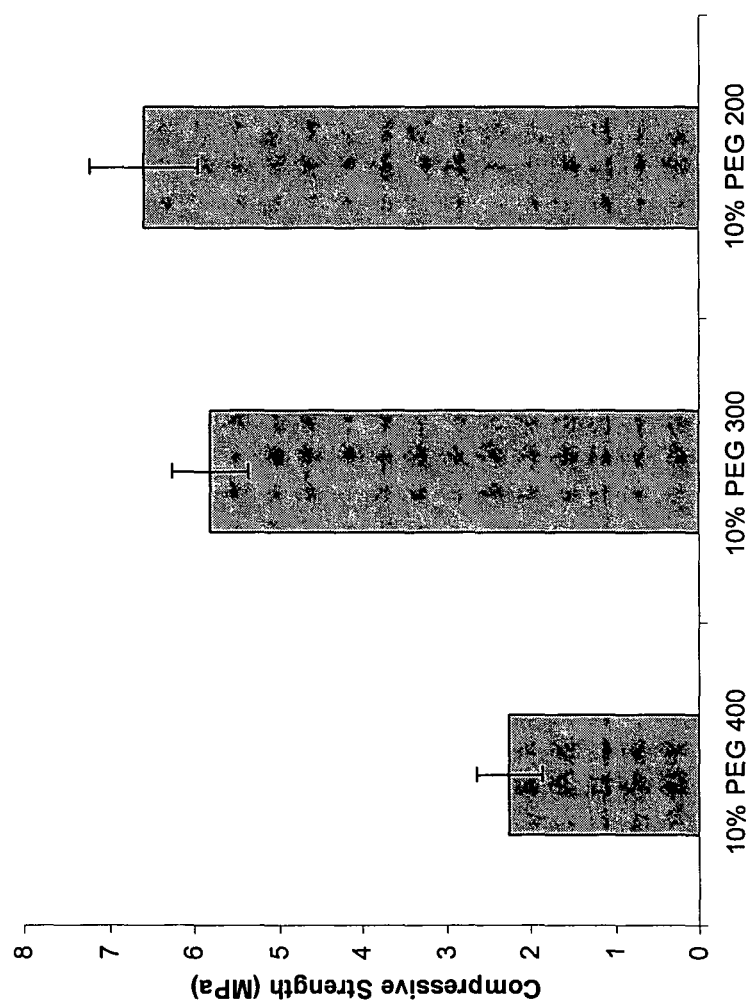
FIG. 4 illustrates the compressive strength values for PLGA scaffolds containing 10% PEG at three different molecular weights after being submerged for 24 hours in distilled water.

The results are shown in FIG. 4. The value for each fracture point is given as the compressive strength of the scaffold in mega pascals (MPa).

Conclusions

It can be concluded that the compressive strength of the scaffolds increases with decreasing PEG molecular weight. This is believed to be a result of the smaller PEG molecules leaching more rapidly from the scaffolds resulting in an increase in the glass transition temperature of the PLGA.

The invention claimed is:

1. An injectable composition administrable to a human or non-human animal consisting of polymer particles capable of cross-linking and an aqueous carrier, wherein the polymer particles consist of a first polymer and a second polymer,
   wherein the first polymer is a plasticizer having a molecular weight of 800 Da or less and is soluble or dispersible in the carrier, such that 1 wt % or more of the first polymer will leach into the carrier within 20 hours at 25° C. immediately after combining the first and second polymers with the carrier,
   wherein the second polymer is an amorphous or semi-crystalline polymer,
   wherein the amount of the first polymer present in the polymer particles is from 1 to 20% by weight and the ratio of polymer to carrier is from 4:1 to 1:4,
   wherein the polymer particles have a glass transition temperature lower than the glass transition temperature of the second polymer on its own,
   wherein the polymer particles cross-link in vivo by one or more of fusion, adhesion, cohesion, and entanglement to form a scaffold of polymer particles; and
   wherein removal of the first polymer from the scaffold of polymer particles in vivo by leaching results in a hardened scaffold structure.

2. The composition of claim 1, wherein the polymer particles have a glass transition temperature of 45° C. or less.

3. The composition of claim 2, wherein the polymer particles have a glass transition temperature of 37° C. or less and wherein the glass transition temperature of the polymer particles is lower than the glass transition temperature of the second polymer particle on its own.

4. The composition of claim 1, wherein the plasticizer having a molecular weight of 800 Da or less is selected from the group consisting of: polyethylene glycol (PEG), poly(propylene adipate) (PPA), polyt(butylene adipate) (PBA), poly lactic acid (PLA), polyglycolic acids (PGA), poly(D,Lvlactide-co-glycolide)(PLGA), poly propylene glycol, poly capralactone, polyethylene glycol polypropylene block co-polymers.

5. The composition of claim 4, wherein the plasticizer having a molecular weight of 800 Da or less is PEG.

6. The composition of claim 5, wherein the plasticiser is PEG having a molecular weight of 400 Da or less.

7. The composition of claim 1, wherein the amount of the first polymer present in the polymer particles is from 3% to 10% by weight.

8. The composition of claim 1, wherein the second polymer is selected from the group comprising poly lactic acid (PLA), polyglycolic acids, poly(D,L-Iactide-co-glycolide)(PLGA), poly D,L-Iactic acid (PDLLA), poly-Iactide poly-glycolide copolymers and combinations thereof.

9. The composition of claim 7, wherein the first polymer is PEG and the second polymer is PLGA.

10. A kit for use in producing a tissue scaffold comprising a composition according to claim 1, instructions to use the composition, and optionally further comprising a syringe for use in injecting the composition.

11. A method of producing a scaffold in vivo in a human or non-human animal, comprising:
   (a) administering an injectable composition according to claim 1 to a human or non-human animal.

12. The method of claim 11, wherein the polymer particles have a glass transition temperature of 45° C. or less.

13. The method of claim 12, wherein the polymer particles have a glass transition temperature of 37° C. or less and wherein the glass transition temperature of the polymer particles is lower than the glass transition temperature of the second polymer particle on its own.

14. The method of claim 11, wherein the plasticizer having a molecular weight of 800 Da or less is selected from the group consisting of: polyethylene glycol (PEG), poly (propylene adipate) (PPA), polyt(butylene adipate) (PBA), poly lactic acid (PLA), polyglycolic acids (PGA), poly(D,Lvlactide-co-glycolide)(PLGA), poly propylene glycol, poly capralactone, polyethylene glycol polypropylene block co-polymers.

15. The method of claim 14, wherein the plasticizer having a molecular weight of 800 Da or less is PEG.

16. The method of claim 15, wherein the plasticiser is PEG having a molecular weight of 400 Da or less.

17. The method of claim 11, wherein the amount of the first polymer present in the polymer particles is from 3% to 10% by weight.

18. The method of claim 11, wherein the second polymer is selected from the group comprising poly lactic acid (PLA), polyglycolic acids, poly(D,L-Iactide-co-glycolide) (PLGA), poly D,L-Iactic acid (PDLLA), poly-Iactide polyglycolide copolymers and combinations thereof.

19. The method of claim 17, wherein the first polymer is PEG and the second polymer is PLGA.

* * * * *